United States Patent [19]

Argaud

[11] Patent Number: 5,482,413
[45] Date of Patent: Jan. 9, 1996

[54] PNEUMATIC TOOL

[75] Inventor: Pierre-Yves Argaud, Evian, France

[73] Assignee: Etablissements Charles Maire, Evian Cedex, France

[21] Appl. No.: 231,829

[22] Filed: Apr. 25, 1994

[30] Foreign Application Priority Data

May 6, 1993 [FR] France .................................. 93 05462

[51] Int. Cl.⁶ .............................. B23B 45/04; A61C 1/08
[52] U.S. Cl. ..................... 408/124; 408/239 R; 408/702; 403/349; 433/126
[58] Field of Search ............................. 408/124, 239 R, 408/239 A, 702; 403/4, 349; 433/126, 130, 132, 133

[56] References Cited

U.S. PATENT DOCUMENTS

| | | |
|---|---|---|
| 3,574,374 | 4/1971 | Kellar et al. . |
| 3,835,858 | 9/1974 | Hagen . |
| 4,286,951 | 9/1981 | Leonard . |
| 4,493,646 | 1/1985 | Lacour et al. . |

FOREIGN PATENT DOCUMENTS

| | | |
|---|---|---|
| 2445134 | 7/1980 | France . |
| 2660886 | 10/1991 | France . |

*Primary Examiner*—Steven C. Bishop
*Attorney, Agent, or Firm*—Sandler, Greenblum & Bernstein

[57] ABSTRACT

A pneumatic tool comprises a motor element including a body in which a pneumatic motor is housed. The body is connected at one end to a compressed air supply hose together with a device for controlling the entry of compressed air into the motor. At the other end is a head provided with a bayonet coupling and a tool-holder having a tubular member guiding a shaft coupled to the motor. The tool-holder is provided at one end with a complementary bayonet coupling and at the other end with an angular part provided with a member adapted to support a tool. This member is coupled by a kinematic coupling to the shaft. The tubular member guiding the shaft is mounted to pivot relative to the shaft on the complementary bayonet coupling. The tubular member can be locked in any appropriate angular position.

3 Claims, 3 Drawing Sheets

5,482,413

PNEUMATIC TOOL

BACKGROUND OF THE INVENTION

1. Field of the Invention

The present invention concerns a pneumatic tool.

The present invention is directed to pneumatic tools which comprise a body in which a pneumatic motor is housed, said body having at one end means for connecting it to a compressed air supply hose while the other end is fastened to a tool-holder terminating in an angular part receiving a tool, for example a chuck for gripping a drill bit.

2. Description of the Prior Art

Some screwing, unscrewing, drilling, etc jobs have often to be carried out in inaccessible places and the angular parts can have various shapes, for example bent at 90° or 120° or bent once at 90° and again at 90°. Consequently, a series of pneumatic tools must be made available, according to the nature of the jobs to be undertaken. This is costly and somewhat impractical. A first object of the invention is to solve this problem.

These pneumatic tools usually include a lever articulated to the body and controlling the feed of compressed air to the motor, the body being held against the palm of the hand of the user and the lever being actuated by the fingers. The angular part is very often not suitably oriented relative to the lever for the job at hand and this obliges the worker to contort the hand which is tiring and detrimental to the quality of the work to be done.

The prior art includes U.S. Pat. No. 3,574,374 which is directed to a surgical instrument which comprises a motor element and a tool-holder terminating in an angular part adapted to receive a tool.

The motor element terminates at a bush having axial guide slots and a groove while the tool-holder has at the corresponding end a male part adapted to be inserted into the bush and having a lateral projection adapted to be selectively engaged in a slot of the bush and a ball catch which cooperates with the groove to fix the tool-holder to the motor element.

With an instrument of this kind the angular position of the tool-holder relative to the motor element can be changed, subject to a limitation set by the number of guide slots. Also, modifying the angular position necessarily entails uncoupling the tool-holder and the motor element.

The instrument described in this American patent cannot feasibly provide a U-shaped tool-holder, i.e. a tool-holder in which the part holding the tool is on the same side as the male part adapted to be inserted in the bush, because during use the tool-holder would be uncoupled from the motor element.

One object of the invention is to remedy the drawbacks of the prior art.

SUMMARY OF THE INVENTION

A pneumatic tool in accordance with the invention comprises a motor element including a body in which a pneumatic motor is housed, said body including at one end means for connecting it to a compressed air supply hose together with means for controlling the feed of compressed air to the motor and, at the other end, a head provided with bayonet coupling means and a tool-holder having a tubular member guiding a shaft provided with means for coupling it to said motor, said tool-holder being provided at one end with means complementary to the bayonet coupling means of said head and at the other end with an angular part provided with a member adapted to support a tool, said member being coupled by a kinematic coupling to said shaft, in which tool said tubular member guiding said shaft is mounted to pivot relative to said shaft on said complementary bayonet coupling means, means being provided for locking said tubular member in any appropriate angular position.

In this way the angular part can easily be oriented relative to the means controlling feed of compressed air to the pneumatic motor and consequently the user can always hold the body in the most appropriate position to carry out a given operation.

By virtue of one feature of the invention said complementary bayonet coupling means of said tool-holder comprise a bush extended by a skirt adapted to cap said head and provided internally with pegs adapted to cooperate with ramp surfaces of said head, said bush being engaged on said tubular member and bearing against an abutment thereof, a compression spring surrounding said tubular member being inserted in a housing in said bush and one end of said compression spring bears against the far end of said housing and the other end of said compression spring bears against a washer mounted on said tubular member and carrying pins adapted to cooperate with spot-faced recesses at the corresponding end of said head which are regularly offset in the circumferential direction.

By virtue of a specific feature of the invention said tubular member includes a shoulder incorporating holes through which said pins pass.

By virtue of another feature of the invention each ramp surface includes at least two notches with which said pegs of said bush selectively cooperate, a first notch corresponding to a position in which said spring is not compressed, so that said tubular member can turn, and a second notch corresponding to a position in which said spring is compressed to lock said tool-holder.

The invention is now described in more detail with reference to specific embodiments given by way of example only and shown in the appended drawings.

DETAILED DESCRIPTION OF THE PREFERRED EMBODIMENTS

Figure 1:
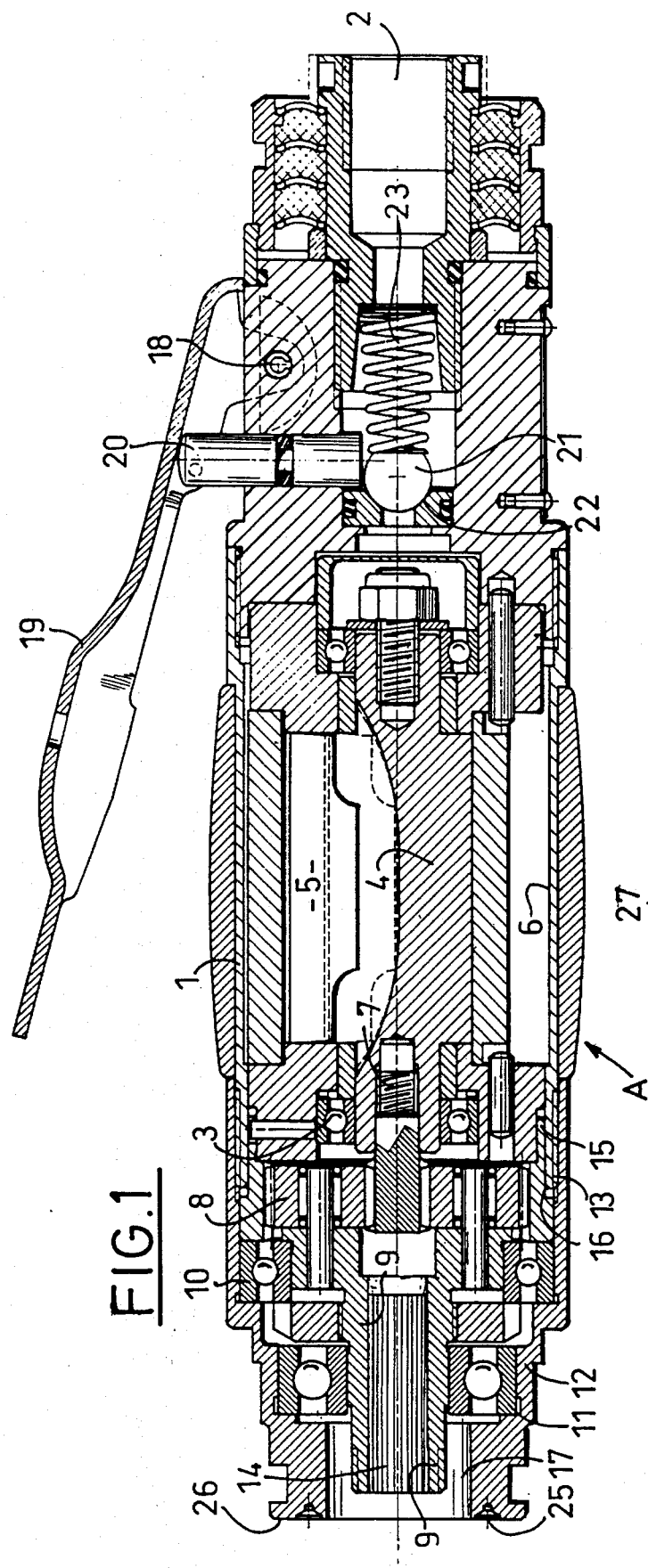
FIG. 1 is an axial cross-sectional view of the motor element.

The tools shown in the figures comprises a motor element A and tool-holders B.

The motor element A has a body 1 with a connector 2 at one end adapted to be connected to a compressed air supply hose.

A rotor 4 of a pneumatic motor is mounted in the body 1 on bearings 3. The motor has vanes 5 cooperating with the interior lateral surface of a cylinder 6.

The rotor 4 is fastened to a gear 7 driving through two planet wheels 8 and a toothed ring 15 a planet-wheel-holder 9 rotating in bearings 10 and 11 housed in a head 12 which has an internal thread 13 screwed on to an external thread 16 of the body 1.

The coupling sleeve 9 has splines 14.

A handle 19 is hinged to the body 1 about a pivot pin 18. The handle has a plunger 20 adapted to cooperate with a ball valve 21 spring-loaded onto its seat 22 by a compression spring 23. The handle 19 is adapted to control the feed of compressed air to the pneumatic motor.

Figure 2:
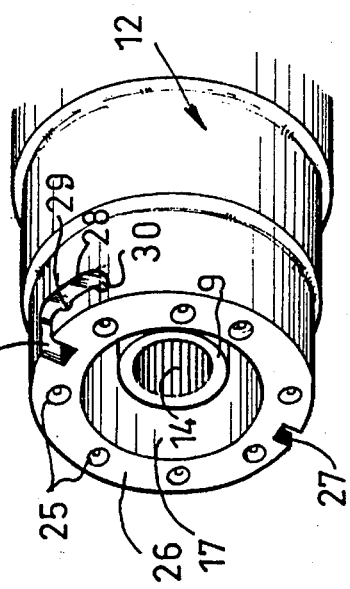
FIG. 2 is a perspective view of one end of the motor element.

The head 12 (see FIG. 2) has a central hole 17 and on its free surface 26 a series of machined portions 25 which are regularly offset in the circumferential direction and constitute abutments for the tool-holder B, as explained below.

The free surface 26 also has two lateral slots 27 offset by 180° in the circumferential direction and opening into ramp surfaces 28 inclined towards the rear end of the motor element A and having a first notch 29 and a second notch 30.

Figure 6:
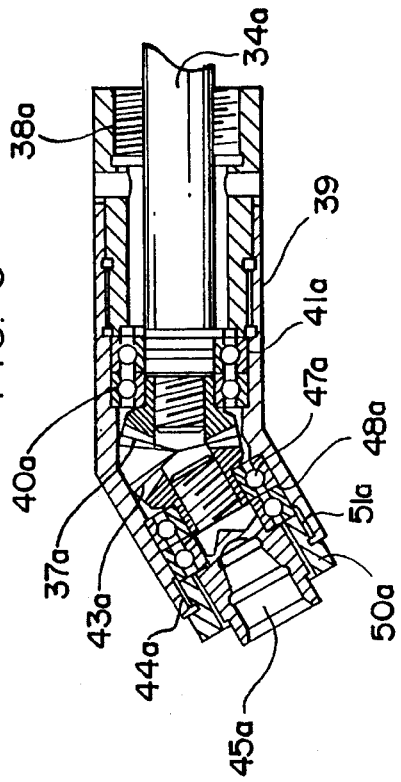
FIGS. 6 and 7 are cross-sectional views of different tool-holders.
Figure 4:
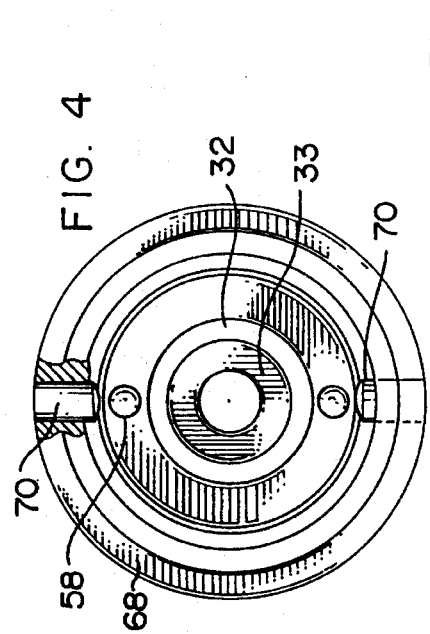
FIG. 4 is an elevation view of the end of the tool-holder adapted to be coupled to the motor element.
Figure 7:
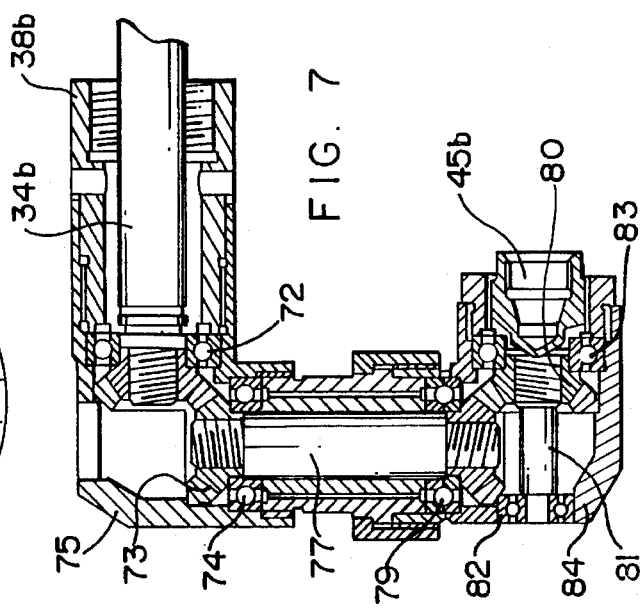
Figure 5:
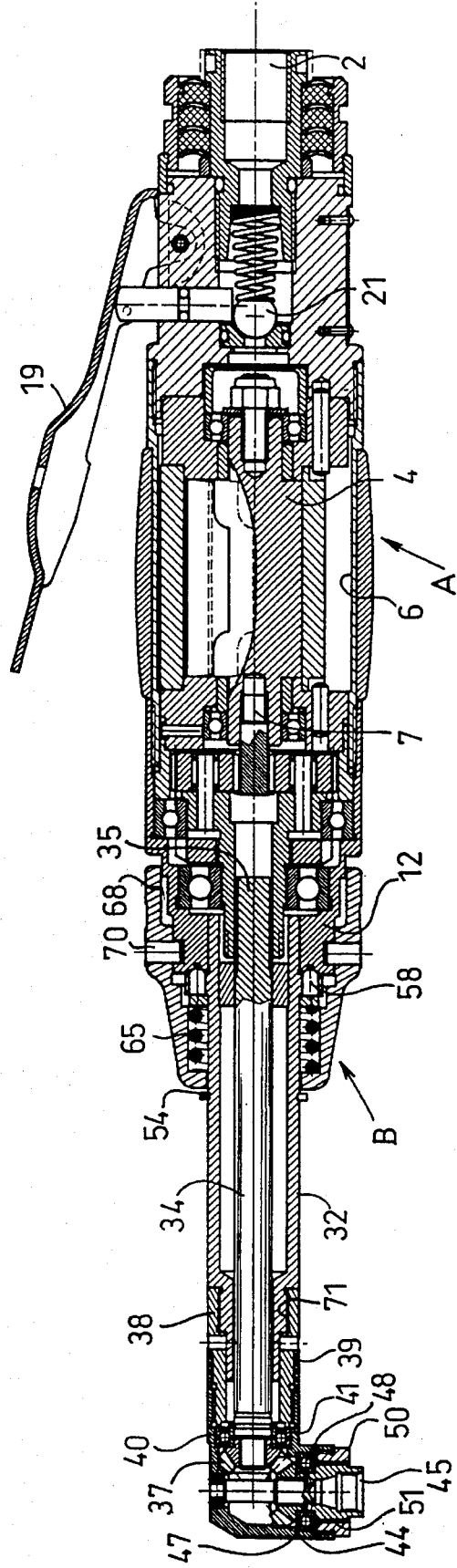
FIG. 5 shows the motor element and the tool-holder mounted on it in axial cross-section.

The body 1 is adapted to receive, selectively, tool-holders such as those shown in FIGS. 5, 6 and 7.

Figure 3:
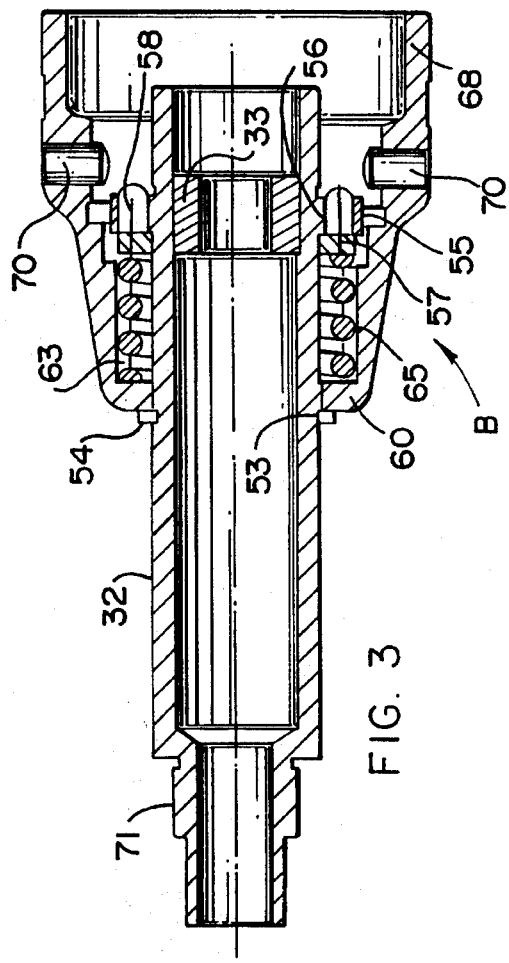
FIG. 3 shows part of the tool-holder in axial cross-section.

FIG. 3 shows part of a tool-holder B which comprises a tubular member 32 near one end of which is mounted a bearing 33. The other end has a screwthread 71.

An abutment 54 is fixed to the tubular member 32, in a groove 53. At the end opposite the screwthread 71 said tubular member 32 has a shoulder 55 in which are two holes 56 offset by 180° in the circumferential direction. A washer 57 is mounted on the tubular member 32. Two pins 58 fastened to it slide in the holes 56.

A bush 60 is mounted on the tubular member 32, between the abutment 54 and the shoulder 55. The bush has a housing 63 in which is accommodated a compression spring 65 surrounding the tubular member 32 and one end of which bears against the far end of the housing 63. Its other end bears against the washer 57.

The bush 60 is extended by a skirt 68 adapted to cap the head 12 and having two radial pegs 70 inside it offset by 180° in the circumferential direction. Each peg is adapted to be inserted in a slot 27 of the head 12 and to cooperate with a respective ramp surface 28; this provides a bayonet coupling so that it is a very simple matter to couple the body 1 to a tool-holder.

Different tool-holders can be based on the element shown in FIG. 3, as shown in FIGS. 5, 6 and 7.

FIG. 5 shows a tool-holder for working at right angles, comprising a shaft 34 guided in the bearing 33 and one end of which has splines 35 adapted to cooperate with the splines 14. The other end receives a bevel gear 37.

Onto the screwthread 71 is screwed a sleeve 38 fastened to an angular sleeve 39 having a bearing surface 41 in which is mounted a ball bearing 40 locked against the far end of the bearing surface 41 by the free end of the sleeve 38.

The bevel gear 37 cooperates with a bevel gear 43 fastened to the inner race 44 of a bearing 48 in which a bush 45 is keyed. The bearing 48 is housed in a bearing surface 47 at the free end of the angular sleeve 39 and retained by a nut 50 screwed into a screwthread 51 of said angular sleeve 39. Said nut 50 is bored to enable the bush 45 to rotate freely.

The bush 45 is adapted to receive a chuck adapted to support drill bits. This chuck could equally well be replaced with tools for screwing or unscrewing screws or nuts of different sizes.

The tool-holder of FIG. 6 is similar to that of FIG. 5, from which it differs by its inclination, which is 150°. This figure uses the same reference numbers as FIG. 5 followed by an "a".

FIG. 7 shows a version of the tool-holder with two bends.

Parts in this figure corresponding to parts in other figures carry the same reference numbers followed by an "a" "b".

A sleeve 38b is screwed to the end of the tubular member 32, on the screwthread 71. A shaft 34b inside the sleeve extends through the tubular member 32 and its free end is splined to cooperate with the splines 14.

The shaft 34b is fastened to a bevel gear 72 which cooperates with a bevel gear 73 guided by a bearing 74 in an angular sleeve 75. The bevel gear 73 is keyed to a shaft 77 whose free end carries a bevel gear 79 cooperating with a bevel gear 80 keyed to a shaft 81 guided in bearings 82 and 83 of a second angular sleeve 84 fastened to the sleeve 75.

The bevel gear 80 is fastened to a bush 45b adapted to receive selectively a tool. The bush 45b extends towards the bush 68 so that when the tool is used the force is applied in a direction tending to uncouple the tool-holder B. However, the tool-holder B cannot be uncoupled inadvertently because of the arrangement according to the invention.

When the tool-holder B is mounted on the motor element A, the splined end 35 of the shaft 34 passes through the hole 17 and is inserted into the coupling sleeve 9, the splines 14 of the latter providing, with those at the end of the shaft 34, a rigid coupling enabling said shaft to be driven.

The bush 68 is mounted on the head by inserting the pegs 70 in the slots 27 after which it is pivoted so that the pins cooperate with the notches 29. In this position the washer 57 is a small distance from the shoulder 55 and the tubular member 32 can be rotated on its shaft to change the angular position of the angular sleeve 39. During this rotation the free ends of the pins 58 which are engaged in the spot-faced recesses 25 escape from the latter against the action of the spring 65 to cooperate with those respective to the selected angular position.

The bush 68 is then tightened so that the pegs 70 arrive at the free end of the ramp surfaces 28 in the notches 30.

When the bush 60 is tightened the angular position of the tubular member 32 is not modified, the shoulder 55 adopting a position near the surface 26 and, the spring 65 being compressed, the pins 58 are engaged in the spot-faced recesses 25 with some force so that the tubular member 32 cannot turn inadvertently.

Of course, the invention is not limited to the embodiments described and shown. Numerous detailed modifications can be made thereto without departing from the scope of the invention.

There is claimed:

1. A pneumatic tool comprising:
   a motor element, said motor element comprising a body housing a pneumatic motor, said body including:
   (a) means for connecting said body to a compressed air supply hose disposed at one end of said body;
   (b) means for controlling the feed of compressed air to said motor; and
   (c) a head provided with bayonet coupling means, said head having a tubular member for guiding a shaft provided with means for coupling said tubular member to said motor;
   a tool-holder disposed at the other end of said body from said connecting means, said tool-holder being provided at one end with means complementary to said bayonet coupling means of said head, and said tool-holder provided, at the other end, with an angular portion provided with a member adapted to support a tool, said member being connected by a kinematic coupling to said shaft, wherein said tubular element for guiding said shaft is pivotally mounted with respect to said shaft on said complementary bayonet coupling means; and means for wedging said tubular member in an angular position, said bayonet coupling means comprising ramps, and said complementary bayonet coupling means comprising pegs cooperating with said ramps, each of said ramps comprising at least two notches with which said pegs cooperate, one of said notches corresponding to a position in which the tubular element can pivot, and the other of said notches corresponding to a position in which said tubular element is wedged.

2. A pneumatic tool according to claim 1, wherein said complementary bayonet assembly means of the tool-holder further comprises:

a bush extended by a skirt adapted to cap said head, said bush comprising pegs adapted to cooperate with said ramps provided on said head, said bush being engaged on said tubular element and bearing against an abutment of said tubular element, said bush disposed in a housing in which a compression spring is inserted circumscribing said tubular element and an end of said spring bears against the bottom of said housing and the other end of said spring bears against a washer mounted on said tubular element, and said bush having pins adapted to cooperate with spot-faced recesses at a corresponding end of said head, said recesses regularly angularly offset.

3. A pneumatic tool according to claim 2, wherein said tubular element includes a shoulder pierced with holes through which said pins pass therethrough.

* * * * *